(12) United States Patent
Buresten

(10) Patent No.: US 7,018,208 B2
(45) Date of Patent: Mar. 28, 2006

(54) DENTAL DEVICE

(75) Inventor: Mats Buresten, Ljungbackenvägen (SE)

(73) Assignee: Milgen Limited, Gibraltar ( * ) Notice: Subject to any disclaimer, the term of this patent is extended or adjusted under 35 U.S.C. 154(b) by 0 days.

(21) Appl. No.: 10/350,412

(22) Filed: Jan. 23, 2003

(65) Prior Publication Data
US 2003/0165797 A1 Sep. 4, 2003

Related U.S. Application Data

(63) Continuation of application No. PCT/SE01/01639, filed on Jul. 16, 2001.

(30) Foreign Application Priority Data
Jul. 24, 2000 (SE) .................................... 0002747

(51) Int. Cl.
*B29C 17/04* (2006.01)
(52) U.S. Cl. ........................ 433/213; 264/552; 425/388
(58) Field of Classification Search ................ 433/213; 264/552, 554; 425/388
See application file for complete search history.

(56) References Cited

U.S. PATENT DOCUMENTS

| 3,072,964 A | * | 1/1963 | Tilden | 425/253 |
| 3,377,656 A | * | 4/1968 | Tilden | 425/388 |
| 3,528,132 A | * | 9/1970 | Greenberg et al. | 425/156 |
| 4,157,884 A | * | 6/1979 | Andrae | 425/173 |
| 4,270,892 A | * | 6/1981 | Faunce | 425/388 |
| 5,667,386 A | | 9/1997 | Black et al. | |
| 5,829,980 A | | 11/1998 | Sheridan et al. | |
| 5,919,418 A | * | 7/1999 | Kendall et al. | 422/28 |

FOREIGN PATENT DOCUMENTS

DE 195 11 064 * 9/1996

* cited by examiner

*Primary Examiner*—Ralph A. Lewis
(74) *Attorney, Agent, or Firm*—Gauthier & Connors LLP

(57) ABSTRACT

A device for the manufacture of a cast, in particular a dental aid from a preheated workable substrate. The device comprises a hollow body having an essentially flat first side being provided with holes which first side is arranged to receive a model from which a cast is to be made. Said first side is adapted to cooperate with a holder-on, which seals the substrate against said first side. The body cooperated with a vacuum source that the cooperation is achieved through one to the body belonging connection being connectably arranged to an external vacuum source.

6 Claims, 3 Drawing Sheets

DENTAL DEVICE

This is a continuation of copending application(s) International Application PCT/SE01/01639 filed on 16 Jul. 2001 and which designated the U.S.

TECHNICAL FIELD

The present invention relates to a device and to a method form producing a cast, in particular dental aids such as gel splints, flooring splints, bleaching splints, soft occlusal splints, temporary crowns and bridges, snoring guards, sport mouth guards, fixing splints for orthodontics, bruxism or the lice.

BACKGROUND OF THE INVENTION

The manufacture of gel splints, flourine splints, bleaching splints, soft occlusal splints, temporary crowns and bridges, snoring guards, sport mouth guards, fixing splints for orthodontics, bruxism or the like, is generally achieved by vacuum forming of a substrate. This is often performed in dental laboratories using complicated equipment, especially as the use of this kind of devices for security reasons are not allowed in the dental surgery room next to the patient. The heating of the substrate is often performed with electricity and generates heat, which may ignite volatile substances and gases present in the dental surgery room and even cause explosions. Additionally, harmful agents may be released from the polymer used to form the dental aids. The equipments from the prior art often generate noise and odours.

Since it is awkward and time consuming to achieve the dental aids using this kind of equipment, it will lead to a decreased possibility for the dental clinics to be able to produce these dental aids.

U.S. Pat. No. 5,667,386, for example, discloses such a device using vacuum from an internally arranged vacuum pump and electrical heating coils for heating the substrate for the production of a dental aid. The document describes a method for the posttreatment of a moulded substrate obtained by a device described above. The substrate which will be formed after the teeth model is preheated using electrical heating coils before it is being applied over the model. The final shape of the cast is obtained by means of a membrane arranged on a holder-on. The use of electrical heating coils to heat the substrate before the forming, does not make the thickness of the final product equal, since a temperature gradient arises in the substrate, using this kind of heating. This kind of device and the method of posttreating a substrate involves a complicated equipment and many process steps. There is also a risk that volatile components are released from the polymer at the heating stage. The maintenance of the instrument is also difficult, due to all its parts. In addition, residual pieces of plastics are liable to get stuck into the instrument.

Since this instrument for security reasons are not allowed to be used in the dental surgery room, there exists a need for a simple and cheap device which may be used directly next to the patient. This device should comprise few parts, being easy to handle and not be powered electrically and have an internally arranged vacuum pump. It must be allowed to be used in the dental surgery room and at the same time provide a product having the desired properties such as an even thickness.

SUMMARY OF THE INVENTION

The object of the present invention is to provide a dental device and a method for the production of gel splints, flooring splints, bleaching splints, soft occlusal splints, temporary crowns and bridges, snoring guards, sport mouth guards, fixing splints for orthodontics, etc., for dental applications which is cheap and can be allowed to be used in the dental surgery room in direct connection to the patient and provides a satisfactory product.

This object is being solved by a device for producing a cast, in particular a dental aid, from a preheated, workable substrate and comprising a hollow body having an essentially flat first side, being provided with holes, said first side is arranged to receive a model from which a cast is to be made, wherein said first side is adapted to cooperate with a holder-on which seals the substrate against said first side, wherein the body cooperates with a vacuum source, characterised in, that the cooperation is achieved by one to the body belonging connection being connectably arranged to an external vacuum source.

It is also provided a method for producing a cast, in particular a dental aid from a preheated, workable substrate, wherein the substrate is being applied on a model from which a cast is to be made, and placed on a first side of a hollow body, which first side is provided with holes and a holder-on is placed over said substrate, to seal said substrate against said first side, whereafter the body cooperates with a vacuum source and the substrate is formed after said model, characterised in, that the cooperation is achieved by one to the body belonging connection being connectable to an external vacuum source.

The device and the method according to the present invention increase the availability for this kind of technique since the present invention utilises a vacuum device, which is required at the manufacture of dental aids, the vacuum device already being in the dental surgery room for other purposes, which makes the manufacture of a dental aid rapid and easy directly next to the patient. This leads to lower costs and trouble for the patient since the adaptation and the manufacture can be performed at the same time. It also leads to lower costs for the clinic and increase the service level of the clinic, since a dentist now may take care of the techniques available and by his own be able to produce the dental aids without needing support from a dental laboratory. Also, from a construction point of view, the present invention provides a simple instrument which is easy to handle and therefore cheap to manufacture as well as to maintain and exhibits a long life. Thus, the device is environment friendly. In addition, the emission of harmful substances to the environment is negligibly low. The present invention also provides a product exhibiting an even thickness compared to devices of the prior art.

BRIEF DESCRIPTION OF THE DRAWINGS

The invention will now be closer described in an embodiment with respect to the enclosed drawings, where.

DETAILED DESCRIPTION OF THE INVENTION

Figure 1:
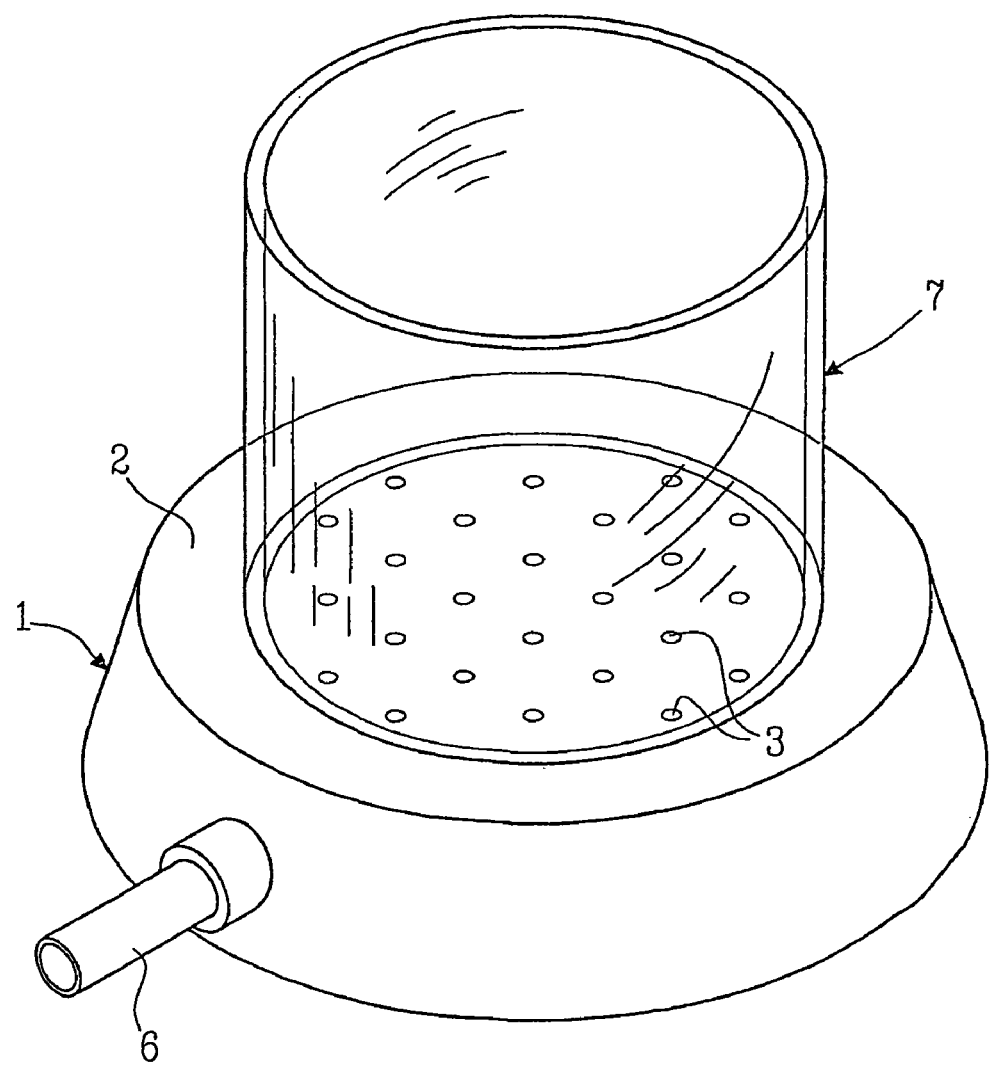
FIG. 1 shows a perspective view of the preferred embodiment according the present invention.

In FIG. 1, the preferred embodiment of the invention is shown. The device comprises a body 1, consisting of a hollow structure and has an essentially round shape. The first side 2 of the body is essentially flat and provided with holes. The holes 3 are equally distributed over said first side 2. The size and the number of the holes 3 are adapted to provide an even negative pressure inside the body. The body is provided with a connection 6, being arranged to be connected to a vacuum source.

Suitably, the body 1 has a round shape but it might also assume other shapes. The body 1 preferably consists of a polymer such as polypropylene, ABS-polymer or another suitable polymer. The body 1 may also be of another material such as a metal, such as pressed steel from acid resistant stainless steel such as SIS 2343, or of aluminium, for example produced by diecasting. Suitably, the body I has a diameter of about 8–25 cm, more preferably between about 10–16 cm.

The connection 6 preferably exhibits a conical shape tapering outwards in a direction from the body 1, which connection 6 is provided with at least one step and preferably, the connection 6 is serrated. Thus, the connection six is adapted to fit existing connections of commercially available Suction devices having different tube diameters. The connection six is provided with O-rings enhancing the sealing against the connecting vacuum source.

The body one has a detachable bottom portion eight, which is sealed against the body by means of a sealing ring, but the bottom portion eight may also be screwed off onto by means of internal threads on the body one. The bottom portion eight may also be adhesively joined to the lower portion of the body. Alternatively the body one could be manufactured in one piece. It could however, be advantageous to be able to remove the bottom portion eight when cleaning the body one.

Figure 2A:
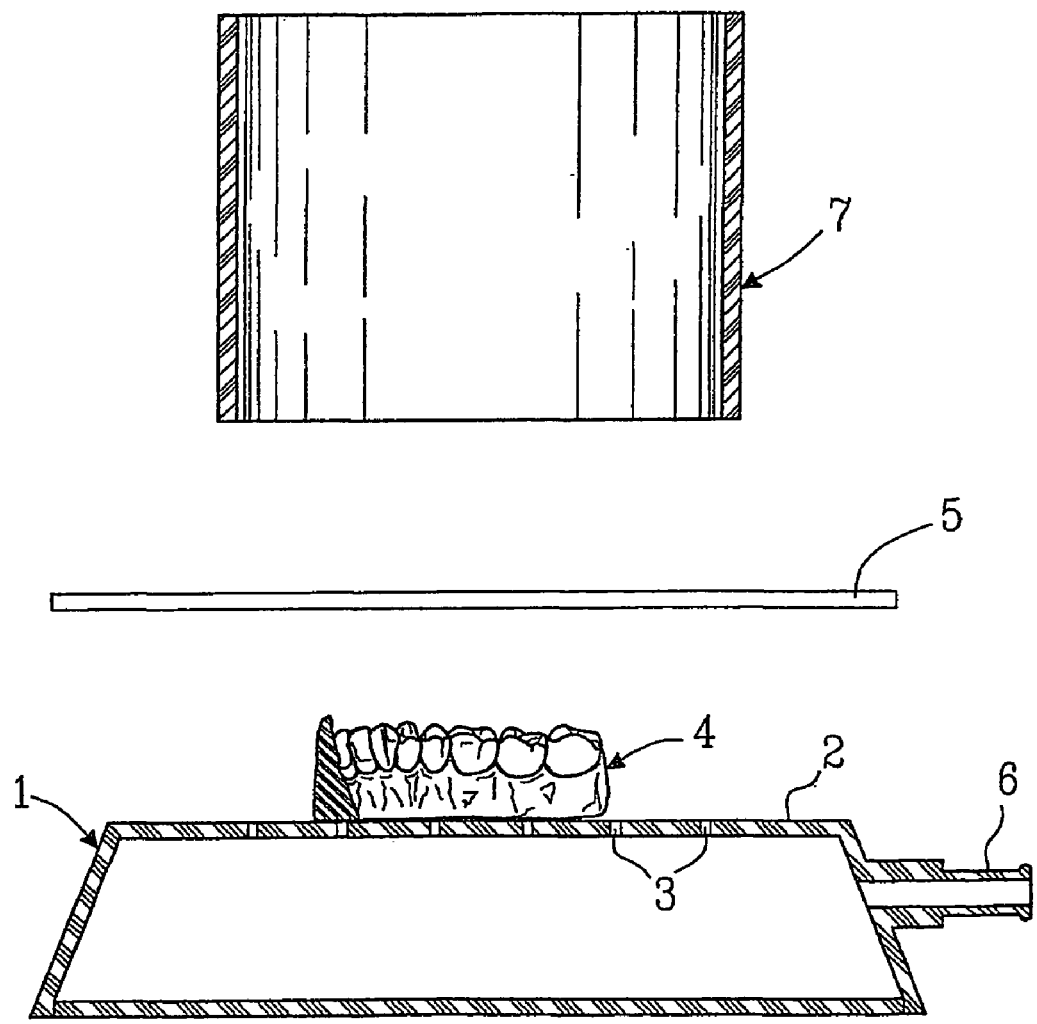
FIGS. 2a–2c show step-by-step how a dental aid is formed by means of the present invention.
Figure 2B:
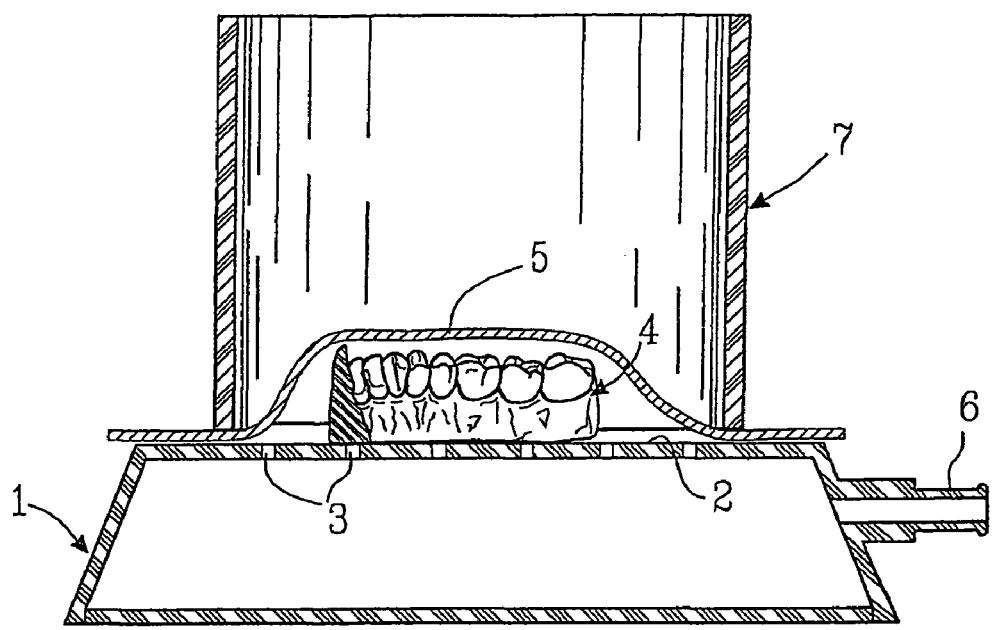
Figure 2C:
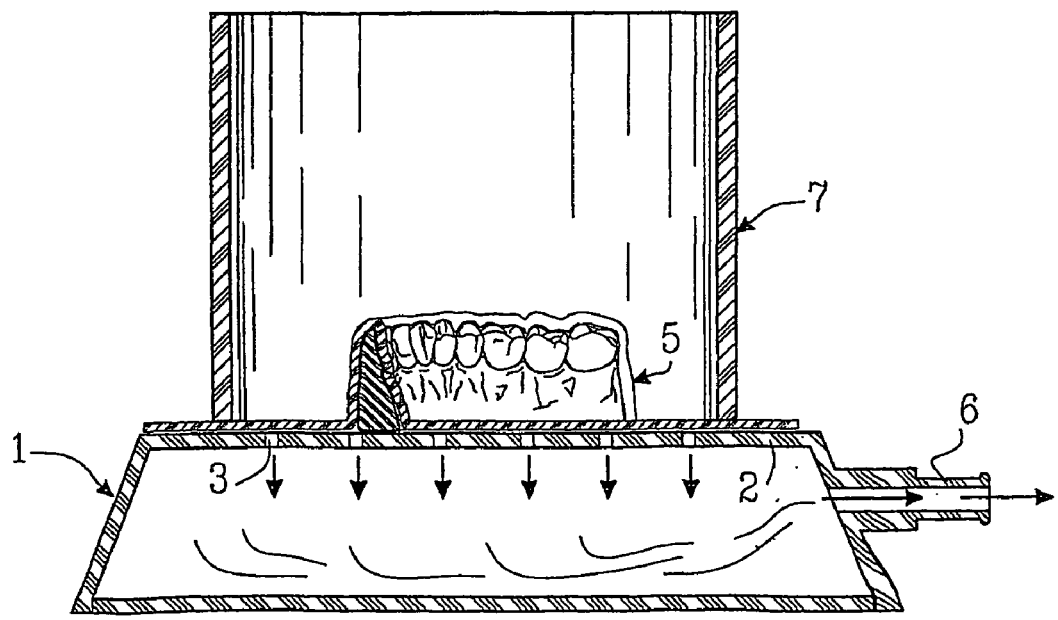

FIGS. 2a–c show step-by-step the manufacture of a dental aid according to a preferred embodiment of the invention. A model 4 representing the teeth of a patient, which model a cast is to be performed from, is placed on said upper side 2. A preheated substrate five is applied over said model, and vacuum is applied through a connection six to the body one. The cylinder 7 is placed over the model 4 and the substrate 5 and is being pressed downwards. The negative pressure formed is sufficient to get the substrate 5 to mould itself after the underlying model 4.

Vacuum is achieved by connecting the body 1 via a connection 6 to a separate suction device of a conventional type (not shown) already being in the dental surgery room. This suction device consists of a vacuum pump being among others being used to suck saliva from the patient's mouth. Thereby is no extra equipment needed to obtain the vacuum required for the moulding of the substrate. In addition, this existing suction device may serve several devices according to the invention in case there are several dentists' chairs in the dental surgery room.

Preferably, preheating of the substrate 5 is performed in a water bath having a temperature up to 100° C. The water bath is of a conventional type (not shown) and is therefore not described in detail here. The waterbath is preferably placed adjacent to the device according to the invention. The temperature in the bath is adapted to the polymer used as substrate. The temperature must be high enough to make the polymer workable. The substrate reaches a temperature being equally distributed over the whole substrate without substantial temperature gradients. The bath could also contain another inert liquid medium giving an equal heating of the substrate.

The substrate 5 could be any workable polymeric material, which is capable of being formed at the above-mentioned condition. The substrate 5 can be a biopolymer or a soft pliable rubber material. It has to be nontoxic and preferably not bind to acrylic material. The substrate 5 will by using the above described method and the device according to the invention produce gel splints, flourine splints, bleaching splints, hard occlusal splints, soft occlusal splints, temporary crowns and bridges, snoring guards, sport mouth guards, fixing splints for orthodontics, etc., for dental applications.

The holder-on 7 preferably consists of a cylinder being open in both its ends. The cylinder has a diameter, suitably making it cover a surface at least corresponding to a surface on said first side 2 being provided with holes and is capable to surround the model, from which a cast is to be done. Thus, the diameter of the cylinder is between about 5 and 20 cm, preferably between about 7 and 11 cm. The cylinder 7 preferably consist of a polymer such as a hexane polymer, but may also be made of other suitable materials such as glass. The holder-on 7 may also have other suitable shapes. The holder-on 7 may for instance be integrated in a device, in which the substrate 5 is arranged, used to hold the substrate 5 in the water bath during the preheating.

EXAMPLE 1

The Manufacture of a Splint

An impression is made from the jaw of a patient. The impression is being filled with plaster in such a way that the model can be directly placed on the device according to the invention for moulding. A sheet of a thermoplastic resin is put using forceps in a water bath having a temperature of about 100° C. for 1 to 2 minutes. The heated polymeric sheet of a thermoplastic resin is transferred to the plaster model and the open cylinder is brought downwards against the first side of the body being connected to the suction device being present in the dental surgery room to among others suck liquid being present in the patient's mouth. After a couple of or minutes moulding under vacuum, the cylinder is put away and the splint is being prepared by cutting the edges and adapt it to the patient.

The invention is not limited to the above described embodiment, but can be varied within the scope of the appended claims.

What is claimed is:

1. A method for the formation of a cast from a pre-heated substrate comprising:
    providing a one-piece housing comprised of a connector integral therewith, said connector being constructed and arranged to communicate with a vacuum source that is externally positioned from said housing, said housing having a perforated top surface;
    providing a one-piece support separate from the substrate and having first and second ends;
    connecting a vacuum source to said connection;
    placing a model on said top surface;
    heating a substrate separate from the one-piece support to form a pre-heated substrate;
    placing said pre-heated substrate over said model;
    placing the second end over said pre-heated substrate; and
    applying a vacuum force through said housing to form a seal between said top surface, said pre-heated substrate and said second end, said vacuum force causing said pre-heated substrate to press into said model to form a cast.

2. The method of claim 1 wherein said one-piece support comprises a cylinder.

3. The method of claim 1 wherein hearing comprises placing at least a portion of said substrate into a water bath.

4. The method of claim 1 wherein said cast is selected from the group consisting of splints, fluorine splints, bleaching splints, hard occlusal splints, soft occlusal splints, temporary crowns, temporary bridges, snoring guards, sport mouth guards and fixing splints for orthodontics.

5. A device for forming a cast from a pre-heated substrate comprising:
   a one-piece support having a first and second end, said support being separate from the substrate while the substrate is pre-heated;
   a one-piece conduit comprised of a perforated top surface, the top surface adapted to receive the one-piece support; and
   a connector integral with said conduit, said connector being configured and arranged to communicate with a vacuum source that is externally positioned from said vacuum conduit the cast being manufactured by placing a model on said top surface, placing the pre-heated substrate under the second end and over the model and applying a vacuum force through said conduit such that a seal is formed between said top surface, the pre-heated substrate and the second end, the applied vacuum force causing the pre-heated substrate to press into the model to form the cast,
   wherein the one-piece support comprises a cylinder.

6. A device for forming a cast from a pre-heated substrate comprising:
   a one-piece support having a first and second end, said support being separate from the substrate while the substrate is pre-heated;
   a one-piece conduit comprised of a perforated top surface, the top surface adapted to receive the one-piece support; and
   a connector integral with said conduit, said connector being configured and arranged to communicate with a vacuum source that is externally positioned from said vacuum conduit, the cast being manufactured by placing a model on said top surface, placing the pre-heated substrate under the second end and over the model and applying a vacuum force through said conduit such that a seal is formed between said top surface, the pre-heated substrate and the second end, the applied vacuum force causing the pre-heated substrate to press into the model to form the cast,
   wherein the one-piece support is comprised of glass.

* * * * *